US008479920B2

(12) United States Patent
Biber

(10) Patent No.: US 8,479,920 B2
(45) Date of Patent: Jul. 9, 2013

(54) PACKAGING FOR DISPOSABLE ABSORBENT PRODUCTS AND RELATED METHODS

(75) Inventor: Mariela Biber, Ardmore, PA (US)

(73) Assignee: SCA Hygiene Products AB, Gothenburg (SE)

( * ) Notice: Subject to any disclaimer, the term of this patent is extended or adjusted under 35 U.S.C. 154(b) by 62 days.

(21) Appl. No.: 13/278,892

(22) Filed: Oct. 21, 2011

(65) Prior Publication Data

US 2013/0098795 A1     Apr. 25, 2013

(51) Int. Cl.
*B65D 73/00* (2006.01)
(52) U.S. Cl.
USPC ........................................ 206/459.5; 206/494
(58) Field of Classification Search
USPC .............. 206/438, 440, 494, 812, 459.5, 775, 206/776, 777, 778
See application file for complete search history.

(56) References Cited

U.S. PATENT DOCUMENTS

| | | | |
|---|---|---|---|
| 6,318,555 B1 | 11/2001 | Kuske et al. | |
| 6,926,149 B2 * | 8/2005 | Tippey | 206/494 |
| 7,021,466 B2 | 4/2006 | Kuske et al. | |
| 7,047,207 B2 | 5/2006 | Stavrulov | |
| 7,185,761 B2 | 3/2007 | Molina et al. | |
| 7,370,760 B2 | 5/2008 | Clough | |
| 7,549,538 B2 | 6/2009 | Naoe et al. | |
| 7,946,420 B2 | 5/2011 | Molina et al. | |
| 7,959,620 B2 | 6/2011 | Miura et al. | |
| 2004/0238393 A1 * | 12/2004 | Ohi et al. | 206/438 |
| 2006/0131200 A1 | 6/2006 | Boldra et al. | |
| 2008/0011642 A1 * | 1/2008 | Oi et al. | 206/778 |
| 2009/0084698 A1 | 4/2009 | Ito et al. | |
| 2009/0088715 A1 | 4/2009 | Ito et al. | |
| 2012/0043244 A1 * | 2/2012 | Hagner et al. | 206/459.5 |

FOREIGN PATENT DOCUMENTS

| | | |
|---|---|---|
| WO | WO 97/49618 A1 | 12/1997 |
| WO | 2004/064872 A2 | 8/2004 |
| WO | WO 2009/040766 A2 | 4/2009 |
| WO | WO 2009/040767 A1 | 4/2009 |

OTHER PUBLICATIONS

Notification of Transmittal of the International Search Report and the Written Opinion of the International Searching Authority, or the Declaration (PCT/ISA/220), PCT International Search Report (PCT/ISA/210) and Written Opinion of the International Searching Authority (Form PCT/ISA/237) issued on Jan. 28, 2013, in corresponding International Application No. PCT/EP2012/070646. (13 pages).

* cited by examiner

*Primary Examiner* — Jacob K Ackun
(74) *Attorney, Agent, or Firm* — Buchanan Ingersoll & Rooney PC

(57) ABSTRACT

A package has a stack of disposable absorbent products in an enclosure defined by a flexible polymer material. The enclosure has top and bottom walls, sidewalls extending between the top and bottom walls, and end walls disposed opposite one another. A compressed stack of disposable absorbent products is located in the interior of the enclosure and exerts an expansion force against the end walls from the interior. The compressed stack includes a first disposable absorbent product contacting one of the end walls, which has a portion that is substantially transparent. The first disposable absorbent product includes a graphic display on an outer surface thereof that faces that end wall. No portion of the graphic display is visible through the substantially transparent portion of that end wall.

20 Claims, 6 Drawing Sheets

US 8,479,920 B2

PACKAGING FOR DISPOSABLE ABSORBENT PRODUCTS AND RELATED METHODS

TECHNICAL FIELD

The present invention is generally related to absorbent products and, more particularly, to packaging for disposable absorbent products that are worn by humans for the containment and absorption of fluid bodily secretions.

BACKGROUND

Disposable absorbent products for absorption of bodily fluids are available in different types, designs, and dimensions. For example, training pants, baby diapers, adult diapers, and incontinence guards are products designed for the containment of urine and excrement. There are other types of disposable absorbent articles, such as feminine hygiene products (e.g., heavy and light incontinence pads, pantiliners) that are designed to contain and absorb urine and/or menses secreted by female wearers. Known products of this type typically include a topsheet facing the body of the wearer, a backsheet facing the garment worn by the wearer, and an absorbent core sandwiched between the topsheet and backsheet.

Products of the type described above are known to be packaged in flexible, polymeric films that completely envelop a stack of the products. These products may be compressed prior to being packaged, and introduced into an open bag formed from the flexible film or otherwise enclosed by the flexible film. The bag or, generally, the film is then typically sealed and the resulting package of disposable absorbent products moved to another stage of the manufacturing process, or to a staging area for further disposition. Often it is desirable to print, on the outer surface of the package, identifying information associated, for example, with a production date, time, and/or other production details of the disposable absorbent products contained in the package. To that end, known processes are known that print identifying information on a transparent portion of one of the walls of the package, for example. In processes of that type for packaging disposable absorbent products that have graphic displays on their outer surfaces, these displays may interfere with the ability of a user or even of manufacturing personnel to read the identifying information. This, in turn, may cause unnecessary delays in the disposition of finished packages or in the overall ability of a user to obtain information associated with the manufacturing of the products contained in the bag.

In addition to the above, packages of disposable products are known that have selected portions that are transparent and other portions that are opaque. Further, transparent portions are known to provide certain advantages, such as allowing the buyer to see a general shape, feature, or predominant color of the product contained in a package resting on a store shelf, or permitting the user to see the number of products left in a package. But transparent portions may offer certain disadvantages. For example, in the case of products made for children, the transparent portions may eliminate the element of surprise that children arc known to appreciate, by easily disclosing the graphic displays that are present on the product.

Accordingly, it is desirable to provide a package of disposable absorbent products, and related methods, that address these and other drawbacks of conventional packages.

BRIEF DESCRIPTION OF THE DRAWINGS

The objectives and features of the invention will become more readily apparent from the following detailed description taken in conjunction with the accompanying drawings in which.

SUMMARY

Figure 1:
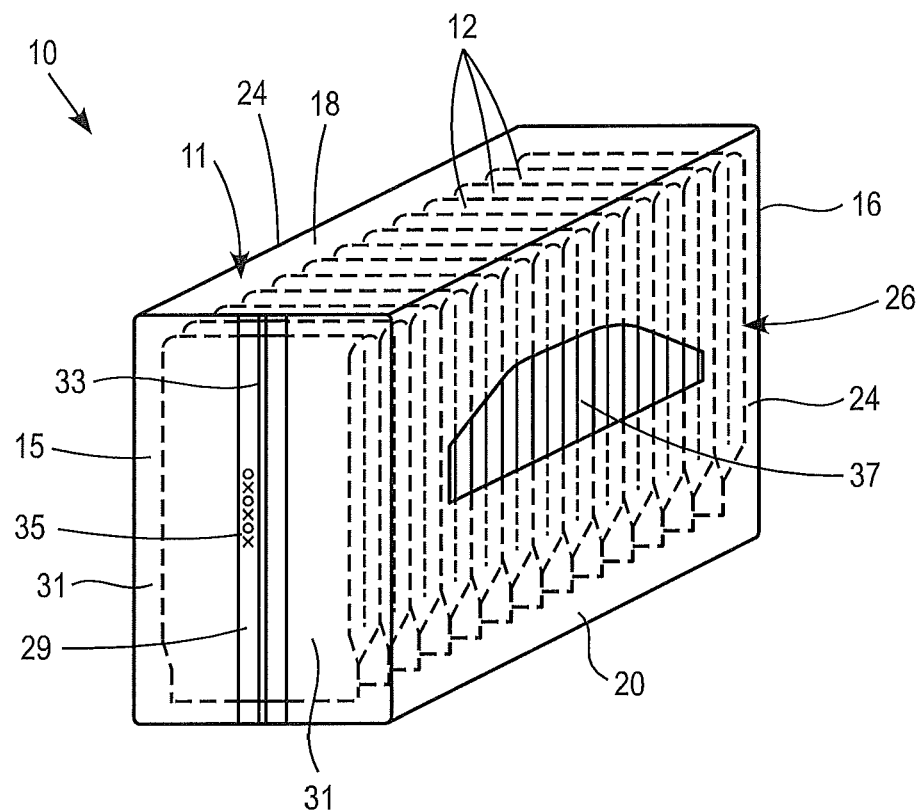
FIG. 1 is a perspective view of a package of disposable absorbent products in accordance with one embodiment of the invention.

In one embodiment, a package of disposable absorbent products is provided that includes an enclosure defined by a flexible polymer material. The enclosure has an interior, and includes a top wall, a bottom wall disposed opposite the top wall, first and second sidewalls disposed opposite one another and extending between the top and bottom walls, and first and second end walls that are disposed opposite one another. The package also includes a compressed stack of disposable absorbent products in the interior of the enclosure and which exerts an expansion force against the end walls from the interior.

The compressed stack includes a first disposable absorbent product contacting the first end wall from the interior, and a second disposable absorbent product contacting the second end wall from the interior. The first end wall in this embodiment has a portion that is substantially transparent. In addition, the first disposable absorbent product includes a graphic display on an outer surface thereof that is in contact with the first end wall. In this embodiment, no portion of the graphic display is visible through the substantially transparent portion of the first end wall.

In another embodiment, a package of disposable absorbent products is provided. The package includes an enclosure defined by a flexible polymer material, and which has an interior. The enclosure also has a top wall, a bottom wall disposed opposite the top wall, first and second sidewalls disposed opposite one another and extending between the top and bottom walls, and first and second end walls disposed opposite one another. A compressed stack of disposable absorbent products in the interior exerts an expansion force against the end walls from the interior. The compressed stack includes a first disposable absorbent product contacting the first end wall from the interior. The first end wall has an elongated strip portion that is substantially transparent, and each of the disposable products includes a graphic display on a respective outer surface thereof, with the graphic display of the first disposable absorbent product facing the first end wall from the interior. In this embodiment, no portion of the graphic display of the first disposable absorbent product is visible through the elongated strip portion of the first end wall.

In yet another embodiment, a method if provided for packaging a stack of compressed disposable absorbent products, with at least a first one of the disposable absorbent products being located at an end of the stack having a graphic display on an outer surface thereof. The method includes enclosing the compressed stack with a flexible polymeric material having at least one substantially transparent portion, so as to define an enclosure having an interior and further having a top wall, a bottom wall disposed opposite the top wall, a pair of sidewalls disposed opposite one another and extending between the top and bottom walls, and a pair of end walls. The compressed stack exerts an expansion force against the end walls from the interior. The method also includes positioning the stack and the flexible material relative to one another such that the at least one substantially transparent portion is located at a first one of the end walls of the enclosure such that the graphic display faces the first one of the end walls, and such that no portion of the graphic display is visible through the at least one substantially transparent portion.

DETAILED DESCRIPTION

Figure 1A:
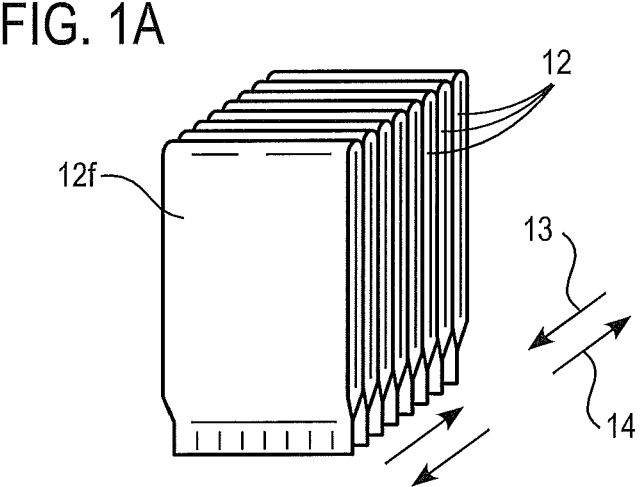
FIG. 1A is a perspective view of a stack of the disposable absorbent products contained in the package of FIG. 1

With reference to the figures, and more particularly to FIGS. 1 and 1A, an exemplary package 10 of disposable absorbent products 12 is illustrated. The package 10 is a generally polyhedral structure (hexahedral in the shown embodiment) that includes an outer, flexible polymeric outer enclosure defining a bag 11 that envelops a stack of the products 12 that are packaged under pressure. For example, and without limitation, the flexible polymeric material defining the bag 11 may be a polyethylene film or film laminate having a thickness of about 2.5 mils (about 0.0635 millimeters). Other non-limiting examples include a LDPE (low density polyethylene) film, a LDPE/LLDPE (linear low density polyethylene) film laminate, a LDPE/MDPE (medium density polyethylene) film laminate, and a LDPE/HDPE (high density polyethylene) film laminate.

The stack of products 12 is packaged under pressure (i.e., they are compression-packed) with a force applied in the general direction of arrows 13. Once the stack of products 12 is in the hag 11, the products 12 exert an outward force (i.e., an expansion force, arrows 14) against a pair of end walls 15, 16 of the package 10. The bag 11 also defines top and bottom walls 18, 20, and a pair of sidewalls 24 extending between the top and bottom walls 18, 20. Package 10 may also include a line of weakness or some other frangible element (not shown) that permits the user to easily tear the bag 11 in specific locations so to gain access to the interior 26 of the bag 11, where the products 12 are located. In specific embodiments, the frangible element is an open-ended arcuate line or a closed geometric shape (e.g., an oval or circle having a perforated perimeter) located entirely within a single one of the walls 15, 16, 18, 20, 24, or extending between at least two adjacent ones of the walls 15, 16, 18, 20, 24.

Package 10 includes, at one or both of the end walls 15, 16, one or more substantially transparent portions and one or more substantially opaque portions. In the illustrated embodiment, the end wall 15 that is shown in the figure has a centrally located, elongated portion 29 that is substantially transparent, and a pair of side portions 31 that are substantially opaque. In addition, package 10 includes a seal 33 extending within the elongated portion 29, and which is formed, in this exemplary embodiment, when sealing a pair of substantially transparent edges of the bag 11. Notably, the package 10 in the shown embodiment also includes indicia 35, such as letters, numbers, symbols, or combinations thereof, printed at the seal 33 or areas adjacent thereto, and which display codified information associated with the products 12 contained in the package 10. For example, and without limitation, the indicia 35 may be a combination of letters and numbers that provide the user or manufacturing personnel with information on the manufacturing facility, manufacturing line, and/or manufacturing date for the products 12. Indicia 35 may also provide information on the available shelf life for the products 12. It is contemplated that indicia 35 may be printed or alternatively embossed, crimped, or through some other method be made to display information associated with the products 12 or some other type of information, all of which is considered to fall within the scope of the present disclosure.

As used herein, the term "transparent" and derivatives thereof refer to the ability of the material to transmit light from the interior of a package to the exterior thereof, so that the products contained in that package may be seen through that material as clearly as if the material were not present. In that regard, a substantially transparent material is a clear film material capable of transmitting light in the range of between about 0% Haze and about 25% Haze, as measured by the ASTM D1003-11 Standard Test Method for Haze and Luminous Transmittance of Transparent Plastics (using either Procedure A—Hazemeter; Procedure B—Spectrophotometer; or the Alternative Haze [Shortcut] Procedure). Moreover, as used herein, the term "opaque" and derivatives thereof refer to the ability of the material to block light from the interior of a package to the exterior thereof, so that the products contained in that package may not be seen through that material. In that regard, a substantially opaque material is capable of substantially blocking light and has opacity in the range from about 55% to about 100%, as measured by the TAPPI T425 Standard Test Method for the Opacity of Paper (average value of 5 specimens when using the 89% reflectance backing or paper backing) or the ASTM D589-97 Standard Test Method for Opacity of Paper (average value of 5 specimens when using the 89% reflectance backing or paper backing). Moreover, a substantially opaque material may be formed from an originally clear film that has ink of a predetermined color (e.g., white) printed thereon or otherwise integrated therewith, or it may instead be originally formed as a colored film.

In another aspect of the embodiment shown in FIG. 1, one of the sidewalls 24 has a substantially transparent portion 37 that permits the user, for example, to assess the number of products 12 that remain in the package 10, or to appreciate other aspects (e.g., shapes, colors) of the products 12 that are not clearly visible through the one or more substantially transparent portions 29 located at one or both of the end walls 15, 16. While not shown, it is contemplated that other substantially transparent portions may be present in package 10, located for example at the top wall 18, bottom wall 20 and/or the other of the sidewalls 24, and which may be present in any number and have any shapes and/or dimensions. For example, it is contemplated that an exemplary substantially transparent portion may extend across two adjacent ones of the walls 15, 16, 18, 20, or 24 or even extend across more than two of the walls.

Figure 2:
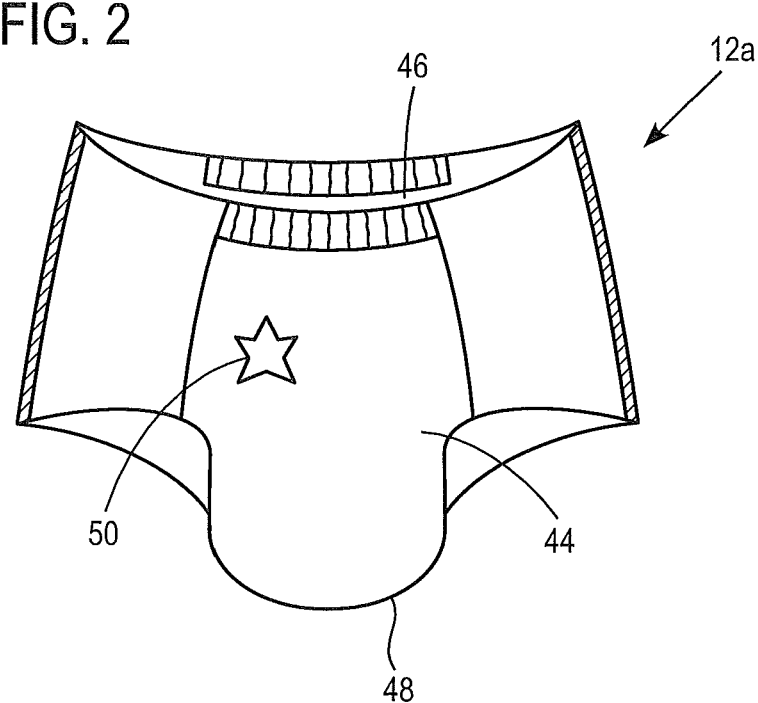
FIG. 2 is an elevation view of an exemplary disposable absorbent product in accordance with one embodiment of the invention.

With reference to FIG. 2, an exemplary product 12a is illustrated. Product 12a is in the form of a training pant, although this is merely exemplary and therefore not intended to be limiting. Product 12a has a front panel 44, a back panel 46, and a crotch panel 48 located between the front and back panels 44, 46. In use, the front panel 44 of product 12a is typically worn on the front side of the wearer (e.g., a child), the back panel 46 is typically worn on the rear side of the wearer, and the crotch panel 48 is typically worn around the crotch area of the wearer. The exemplary product 12a shown in FIG. 2 has a graphic display 50 that is, in the illustrated embodiment, in the form of a single star. It is contemplated, however, that the graphic display 50 may be made up of a single object or shape or a plurality of objects or shapes, such as geometric shapes, representations of an animal or plant or parts thereof, representations of a fictitious or reality-based character, lines, dots, letters, numbers, symbols, or any other regular or irregular objects or shapes or combinations thereof. In that regard, therefore, and as used herein, the term "graphic display" and derivatives thereof refer to a single object or shape, or a plurality of objects or shapes that are similar to or different from one another.

Figure 3:
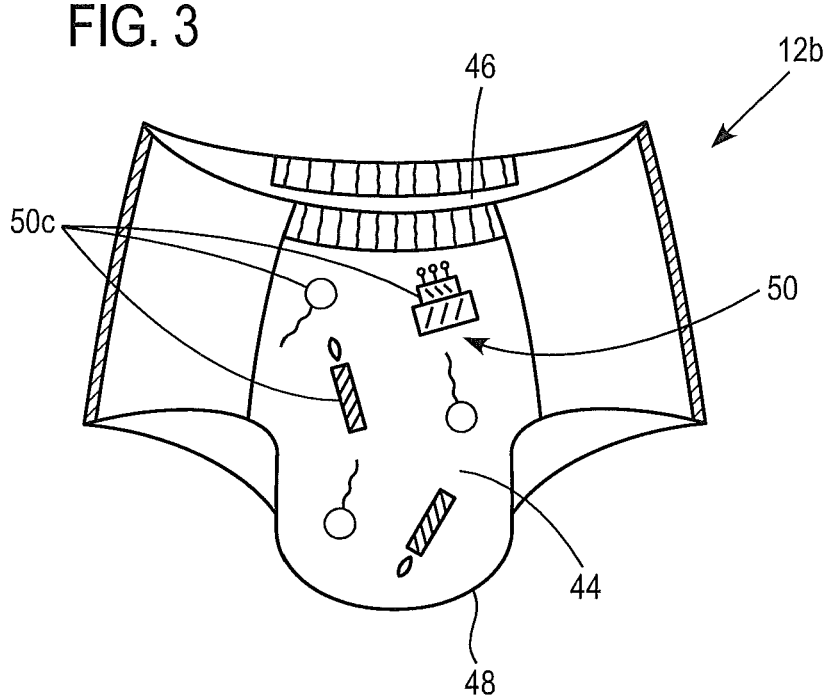
FIG. 3 is a view similar to FIG. 2, showing an exemplary disposable absorbent product in accordance with another embodiment of the invention.

In specific embodiments, the graphic display may for example be a series of objects that are linked by a common theme. For example, and without limitation, FIG. 3, in which like reference numerals refer to similar features in the preceding figures, illustrates a graphic display 50 that is made up of a plurality of figures (e.g., objects or shapes) 50c that are associated with a child's birthday party, such as one or more balloons, one or more birthday candles, and one or more birthday cakes, with each of those figures being either grouped together following a predetermined pattern, or randomly located on the outer surface of the product 12b shown in that figure. It is also understood that the graphic display may be either entirely or partially located on any or all of the panels 44, 46, 48.

Figure 4:
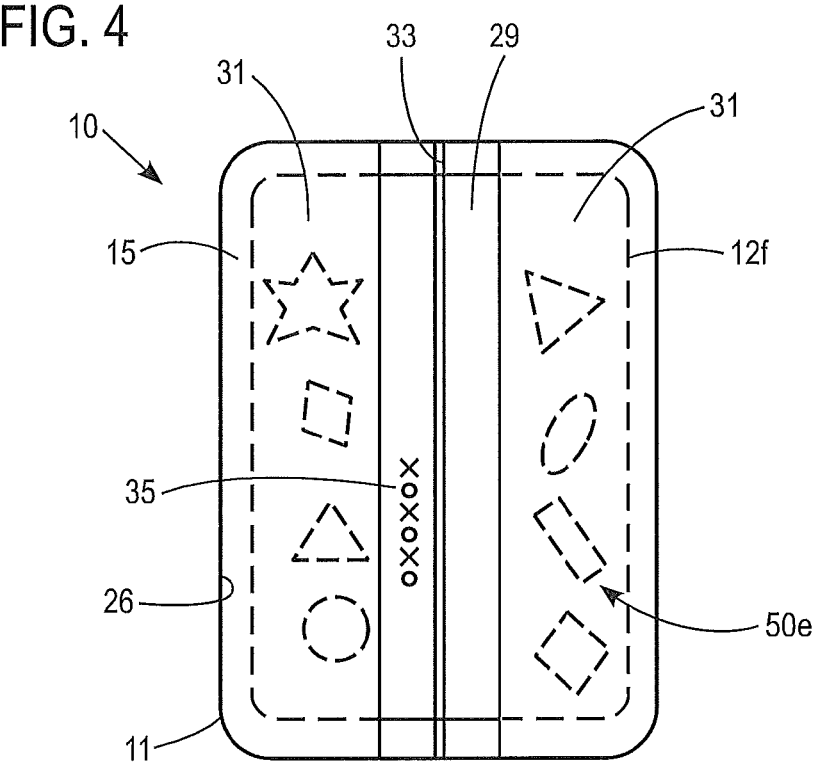
FIG. 4 is an elevation view of the package of FIG. 1, showing a first end wall thereof.

FIG. 4 illustrates an exemplary end wall 15 of the package 10 (FIG. 1). The package 10 shown in FIG. 4 contains, in its interior 26, a stack of products of the general type described above. The package 10 of the illustrated embodiment, and particularly the end wall 15 shown in FIG. 4, are designed such that no portion of the graphic display 50e that is on the outer surface of the first one of the products 12 is visible to the exterior through the substantially transparent portion 29. As that figure shows, the first product 12f in the stack, which is in contact with the end wall 15 from the interior 26, has a graphic display 50e on the surface that faces and contacts the interior surface of the end wall 15. Notably, however, all portions of the graphic display 50e on the first product 12f are hidden from view, by virtue of being in contact with the substantially opaque portions 31, rather than with the substantially transparent portion 29 of the illustrated embodiment.

The substantially transparent portion 29 contains indicia 35 that are easily discernible. More specifically, reading or otherwise obtaining information from the indicia 35 is undisturbed by any of the graphic display 50e that forms part of the first product 12f. In addition to the above, hiding of all portions of the graphic display 50e of first product 12f provides an opportunity to the manufacturer and/or marketer of the products 12 (FIGS. 1, 1A) to pleasantly surprise the user of those products. In the case of children, for example, it may be desirable to hide the graphic display 50e, such that a child wearing the products 12 looks forward, with anticipation, to retrieving additional products 12 from the package 10, so as to be surprised by the graphic display 50e thereon that becomes apparent only upon removal of the product 12 from the bag 11. In that regard, embodiments are contemplated within the scope of the present disclosure, in which each of the products 12 in a package 10 has identical or at least substantially similar graphic displays 50e, or in which the graphic displays 50e vary between products in the stack within a single package 10.

Figure 5:
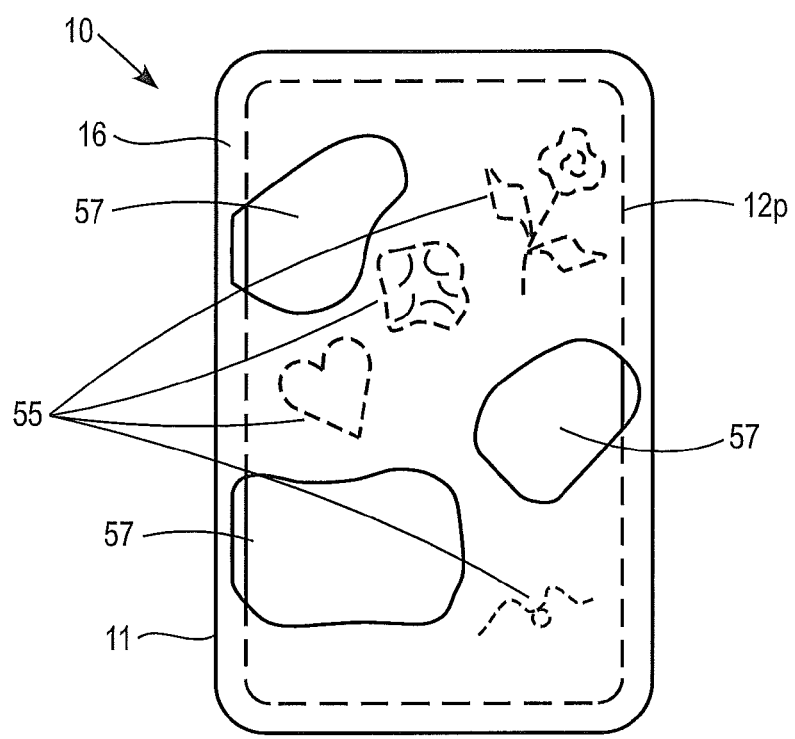
FIG. 5 is a view similar to FIG. 4, showing an exemplary second end wall thereof disposed opposite the first end wall of FIG. 4.

With continued reference to FIG. 4, and further referring now to FIG. 5, the end wall 16 opposite from the end wall 15 shown in FIG. 4 may have a configuration that is similar to or different from that of the end wall 15. More specifically, the entirety of the end wall 16 may be defined by portions of the bag 11 that are substantially opaque, or may have portions that are substantially transparent and having shapes and/or dimensions that are similar to or different from those of substantially transparent portion 29 of end wall 15. Similarly, the stack of products 12 (FIGS. 1 and 1A) in package 10 has a product 12p at the end of the stack that is in contact, from the interior of the package 10, with the interior surface of end wall 16. The product 12p may have a graphic display that is identical or at least substantially similar to the graphic display 50e of the first product 12f. Alternatively, as shown in FIG. 5, the product 12p may have a graphic display 55 that is different from the graphic display 50e on the first product 12f. The end wall 16 in the illustrated embodiment has a plurality of spaced, substantially transparent portions 57 that have a configuration that is different from that of substantially transparent portion 29 at end wall 15 (FIG. 4). Notably, the substantially transparent portions 57 are designed such that no portion of the graphic display 55 is visible therethrough, which also provides the benefits described above with respect to the location of the substantially transparent portion 29 relative to the graphic display 50e of the first product 12f.

While FIGS. 1-5 refer to products 12 that may be in the form of baby diapers or training pants, these are shown and described as such only in exemplary rather than limiting fashion. It is understood, therefore, that the products 12 may instead be in the form of other types of disposable absorbent products such as, and without limitation, adult diapers, incontinence guards, or feminine hygiene products (e.g., heavy and light incontinence pads, pantiliners).

Figure 6:
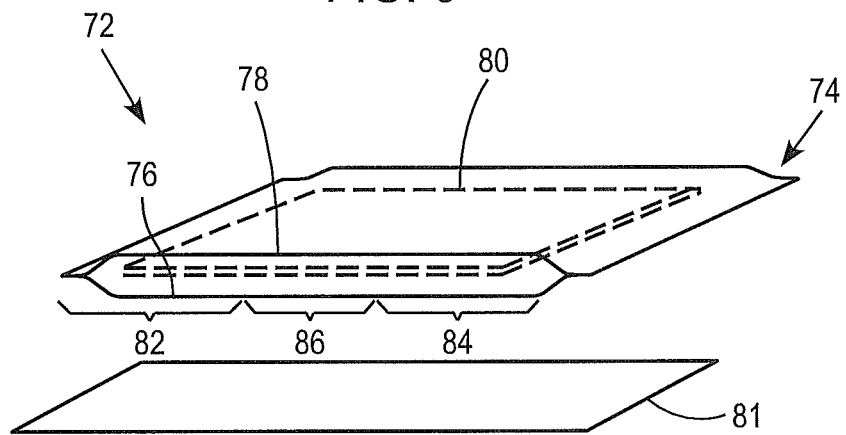
FIG. 6 is a schematic, disassembled view of a disposable absorbent product in accordance with another embodiment of the invention.
Figure 6A:
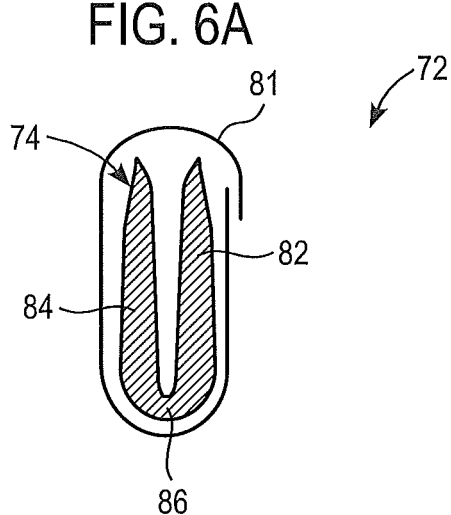
FIG. 6A is a cross-sectional view of the exemplary disposable absorbent product of FIG. 6, in a folded condition, in accordance with one embodiment of the invention.
Figure 6B:
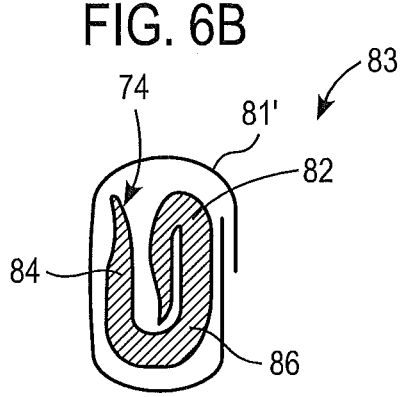
FIG. 6B is a view similar to FIG. 6A, showing the disposable absorbent product of FIG. 6 in a folded condition, in accordance with another embodiment of the invention.

Referring now to FIGS. 6 and 6A, another exemplary product 72 is illustrated, in the form of a catamenial or feminine hygiene product. Product 72 is made up of a body portion 74 comprising a backsheet 76, a topsheet 78, and an absorbent structure or core 80 disposed between the backsheet and topsheet 76, 78, as well as an outer wrapping element 81 that encloses the body portion 74 when folded (FIGS. 6A and 6B). The body portion 74 of product 72 has, in use, a front panel 82 that is predominantly worn on the front side of the wearer (e.g., a woman), a back panel 84 that is predominantly worn on the rear side of the wearer, and a crotch panel 86 that is typically worn around the crotch area of the wearer. For ease of understanding, like reference numerals in FIGS. 6, 6A, and 6B refer to similar features. FIG. 6A illustrates an exemplary folding of the product 72 in which the resulting product is a bifolded structure, enveloped by the outer wrapping element 81. FIG. 6B shows a variation of this embodiment in which a product 83, similar in most respects to product 72, is a trifolded structure enveloped by an outer wrapping element 81'.

In the embodiments illustrated at FIGS. 6A and 6B, each of the exemplary outer wrapping elements 81, 81' has a graphic display 70a, 70b (FIGS. 7 and 8) on its outer surface that includes a plurality of squiggly lines and irregular spots, although these are exemplary and therefore not intended to be limiting.

Figure 7:
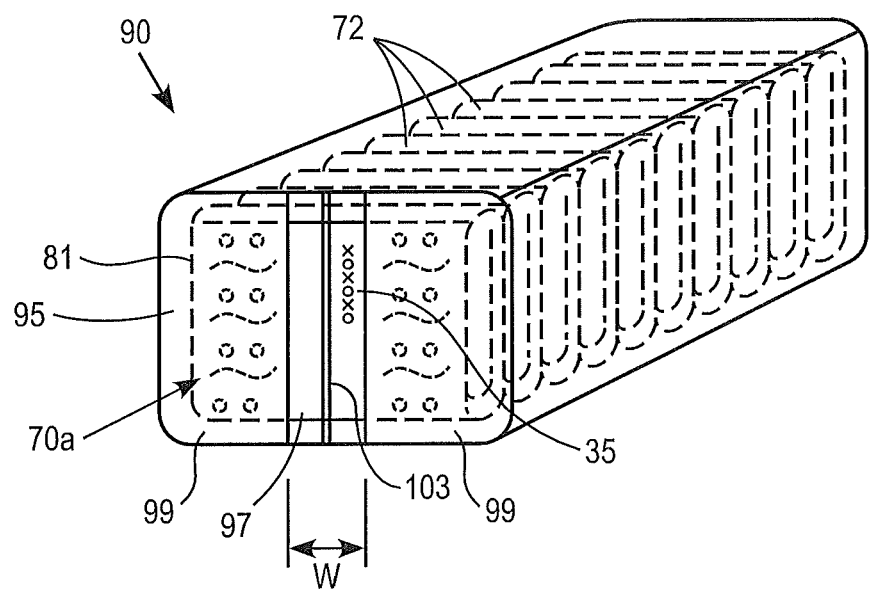
FIG. 7 is a perspective view of a package of disposable absorbent products in accordance with another embodiment of the invention.
Figure 8:
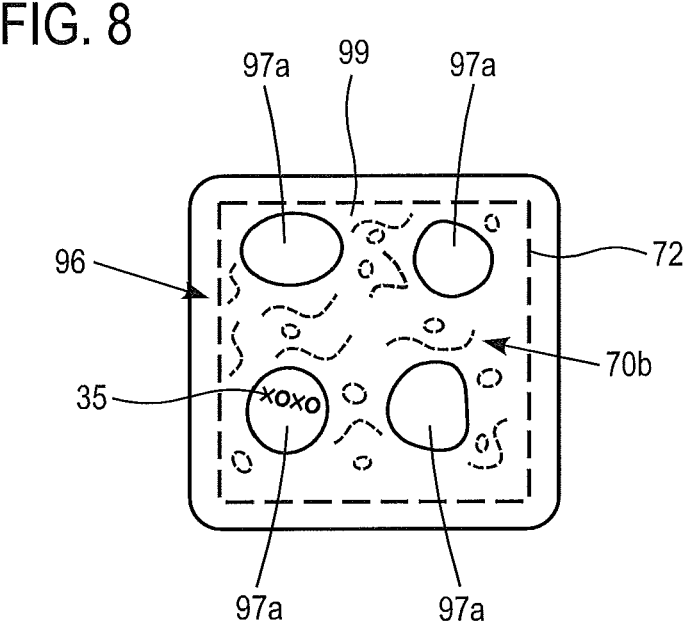
FIG. 8 is an elevation view showing an end wall of a package similar to that of FIG. 7, in accordance with yet another embodiment of the invention.

With reference to FIGS. 7 and 8, an exemplary package 90 is illustrated containing, in its interior, a stack of compressed products 72 (FIGS. 6 and 6A). Those of ordinary skill in the art will readily appreciate that, while package 90 contains products of the type associated with FIG. 6A, it may alternatively contain products similar to the products 83 associated with FIG. 6B, or variations thereof. For ease of understanding, like reference numerals in FIGS. 7 and 8 refer to similar features in any of the preceding figures, the description of which may be referred to for an understanding of the features of the embodiment shown in FIGS. 7 and 8 as well. Package 90 includes an end wall 95 having a substantially transparent portion 97 surrounded by a pair of larger substantially opaque portions 99. In the exemplary embodiment shown in FIG. 7, the substantially transparent portion 97 is in the form of an elongated strip and includes a seal 103, similar to the seal 33 of FIGS. 1 and 4.

The elongated strip-shaped substantially transparent portion 97 in the embodiment of FIG. 7 (or for the substantially transparent portion 29 of FIGS. 1 and 4) may have a width "w," that is no greater than about 25 mm or even no greater than about 7 mm, for example. A variation of this embodiment is contemplated that includes no seal 103 at all, or which instead has a seal or similar structure that is located elsewhere in the package 90. It is also contemplated that the shape and location of the substantially transparent portion 97 on the end wall 95 may be different from that shown in FIG. 7. Yet in another variation, shown in FIG. 8, an end wall 96 may have a plurality of substantially transparent portions 97a that are spaced from one another. In that embodiment, the graphic display 70b of at least the first one of the products in the stack is arranged so as not to be visible through the substantially transparent portions 97a.

In the embodiments of FIGS. 7 and 8, no portion of the graphic display 70a, 70b on the outer wrapping element 81 of the first one of the products 72 (i.e., the product closest to and in direct contact with the interior surface of end wall 95, 96) is visible through the substantially transparent portions 97, 97a. The graphic display 70a, 70b is instead in contact with the substantially opaque portions 99 of the end wall 95, 96. This facilitates reading or otherwise obtaining information from any indicia 35 that may be present at the seal 103 or in any other portion of the substantially transparent portions 97, 97a, as discussed above with respect to the embodiment of FIG. 4. In addition, hiding of the graphic display 70a, 70b behind the substantially opaque portions 99 of the end wall 95, 96 may be desirable in situations in which a marketer or manufacturer of the products 72 wants the potential buyer to see only specific parts or characteristics of the products but not others. For example, a marketer may want the potential buyer to know that the outer wrapping element 81 has a predetermined color e.g., pink, by making that color visible through the substantially transparent portions 97, 97a, while hiding a graphic display 70a, 70b that is present on the surface of the outer wrapping element 81. This may be desirable as a way to pleasantly surprise the user of the product 72 with an unexpected ornamental feature (i.e., the graphic display 70a, 70b) of the products 72. Yet additionally, a marketer may desire to prevent the graphic display 70a, 70b from being visible through one or both of the substantially transparent portions 97, 97a so as to make the package of products 72 discrete, rather than flashy, while making each of the products 72 ornamentally appealing once they are removed from the package.

Figure 9:
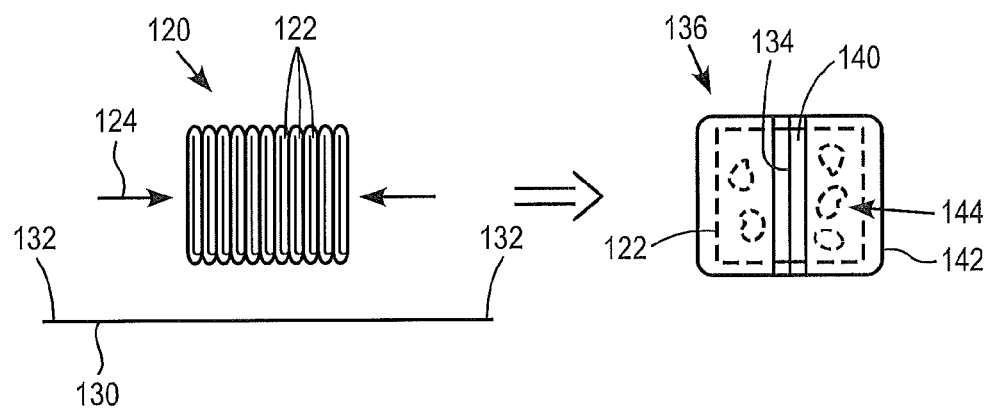
FIG. 9 is a schematic representation of an exemplary process for packaging disposable absorbent products, in accordance with one embodiment of the invention.

With respect to FIG. 9, an exemplary process for packaging a stack of disposable absorbent products is schematically illustrated. The process includes obtaining a stack 120 of disposable absorbent products 122, compressing the stack (arrows 124), and enclosing the compressed stack with a sheet 130 of flexible polymeric material. The sheet 130 is then sealed along a pair of confronting substantially transparent edge portions 132, thereby forming a seal 134 on the finished package 136 of the products 122. The edge portions 132 define an exemplary substantially transparent, elongate portion 140 located at an end wall 142 of the package 136. Notably, this exemplary method includes placing the edge portions 132 relative to the stack 120 such that no portion of a graphic display 144, on at least the first one of the products of the stack 120, is visible through the resulting substantially transparent portion 140 when the package 136 is finally formed.

Figure 10:
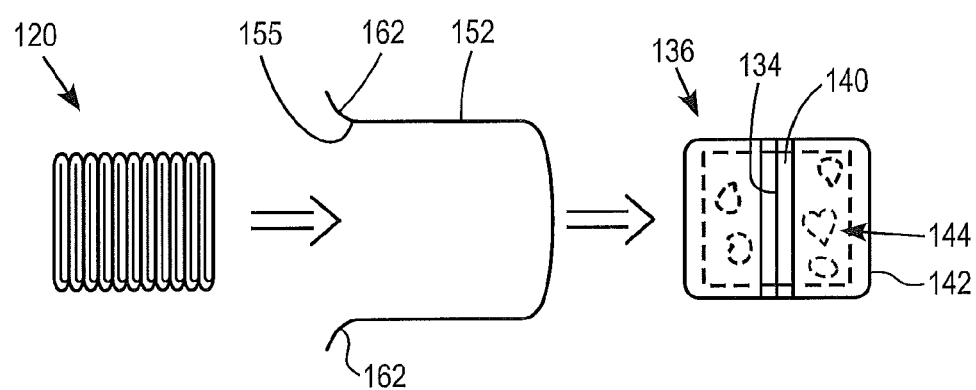
FIG. 10 is a schematic representation of an exemplary process for packaging disposable absorbent products, in accordance with another embodiment of the invention.

A variation of the above-discussed process is schematically illustrated in FIG. 10, in which like reference numerals refer to similar features of the embodiment of FIG. 9. In the process illustrated in FIG. 10, the compressed stack 120 is inserted into a preformed open bag 152 made of a flexible polymeric material. The exemplary preformed bag 152 has an opening 155 that includes substantially transparent edge portions 162. Once the stack 120 is inserted into the open bag 152, same is closed and sealed along the substantially transparent edge portions 162, thereby resulting in the formation of the substantially transparent, elongate portion 140 located at the end wall 142 of the package 136, which may or may not have a seal 134. In this exemplary process, the insertion of the stack 120 into the open bag 152 is such that no portion of the graphic display 144 is visible through the resulting substantially transparent portion 140 when the package 136 is finally formed.

A contemplated variation of the processes described in association with FIGS. 9 and 10 is such that the seal 134 may be located in a different wall, other than one of the end walls of the formed package 136. To that end, the orientation of the stack 120 relative to the sheet 130 (FIG. 9) or open preformed bag 152 (FIG. 10) would be different from that shown in the figures but still fall within the scope of the present disclosure, so long as any transparent portions at one or both of the end walls of the package 136 does not permit the graphic display 144 of an immediately adjacent product 122 to be visible therethrough.

While the above-discussed processes refer to a package 136 in which the resulting transparent portion 140 is in the form of an elongated strip, those of ordinary skill in the art will readily appreciate that the resulting substantially transparent portion 140 of package 136 may have other shapes or dimensions and be present in any number other than one. Similarly, the processes described with respect to FIGS. 9 and 10 are intended to be exemplary rather than limiting, and the products described with respect to FIGS. 1-8 may be packaged by any other suitably chosen methods, so long as they result in packages having the features described in the present disclosure.

Exemplary embodiments of the invention are described as follows, in non-limiting fashion:

1. A package of disposable absorbent products, comprising:
    an enclosure defined by a flexible polymer material, having
        an interior, and including a top wall, a bottom wall disposed opposite said top wall, first and second sidewalls disposed opposite one another and extending between said top and bottom walls, and first and second end walls disposed opposite one another; and a compressed stack of disposable absorbent products in said interior and exerting an expansion force against said end walls from said interior, said compressed stack including a first disposable absorbent product contacting said first end wall from said interior, wherein:

said first end wall has a first substantially transparent portion, said first disposable absorbent product includes a first graphic display on an outer surface thereof facing said first end wall, and no portion of said first graphic display is visible through said first substantially transparent portion of said first end wall.

2. The package of claim 1, wherein said graphic display comprises a plurality of individual figures spaced from one another, none of said figures being visible through the substantially transparent portion of said first end wall.

3. The package of claim 1 or 2, wherein:

said compressed stack has a second disposable absorbent product contacting said second end wall from said interior, said second disposable absorbent product having a second graphic display on an outer surface thereof and facing said second end wall, said second end wall has a portion that is substantially transparent, and no portion of said second graphic display is visible through said substantially transparent portion of said second end wall.

4. The package of claim 3, wherein said first and second graphic displays are at least substantially similar.

5. The package of any of claims 1 to 4, wherein each of said disposable absorbent products in said stack includes a graphic display on a respective outer surface thereof at least substantially similar to said first graphic display.

6. The package of any of claims 1 to 5, wherein said substantially transparent portion is an elongated strip having a width no greater than about 25 mm.

7. The package of any of claims 1 to 6, further comprising identifying indicia on said substantially transparent portion.

8. The package of any of claims 1 to 7, wherein said substantially transparent portion includes a seal of said enclosure.

9. The package of any of claims 1 to 8, wherein at least one of said first or second sidewalls or said top or bottom walls includes a second substantially transparent portion.

10. The package of any of claims 1, 2 or 4 to 9, wherein said second end wall is substantially opaque.

11. The package of any of claims 1 to 10, wherein each of said disposable absorbent products is selected from the group consisting of incontinence pads, feminine pads, training pants, baby diapers, and adult diapers.

12. The package of any of claims 1 to 11, wherein said first disposable absorbent product includes a front panel, a back panel, and a crotch panel between said front and back panels, said first graphic display being located on at least one of said front or back panels.

13. The package of any of claims 1 to 11, wherein said first disposable absorbent product includes a front panel, a back panel, a crotch panel between said front and back panels, and an outer wrapping element enveloping said front, back, and crotch panels, said first graphic display being located on said outer wrapping element.

14. A method of packaging a stack of compressed disposable absorbent products, at least a first one of the disposable absorbent products located at an end of the stack having a graphic display on an outer surface thereof, the method comprising:

enclosing the compressed stack with a flexible polymeric material having at least one substantially transparent portion, so as to define an enclosure having an interior and further having a top wall, a bottom wall disposed opposite the top wall, a pair of sidewalls disposed opposite one another and extending between the top and bottom walls, and a pair of end walls, the compressed stack exerting an expansion force against the end walls from the interior; and positioning the compressed stack and flexible polymeric material relative to one another such that:

(a) the at least one substantially transparent portion is located at a first one of the end walls of the enclosure, (b) the graphic display faces the first one of the end walls, and (c) no portion of the graphic display is visible through the at least one substantially transparent portion.

15. The method of claim 14, further comprising:

defining a seal of the enclosure at the at least one substantially transparent portion.

16. The method of either of claim 14 or 15, further comprising:

displaying information on the substantially transparent portion, the information being associated with the disposable absorbent products contained within the enclosure.

17. The method of any of claims 14 to 16, wherein the flexible polymeric material has at least a second substantially transparent portion, the method further comprising:

positioning the compressed stack and flexible polymeric material relative to one another such that the second substantially transparent portion forms part of at least one of the top wall, bottom wall, or the sidewalls of the enclosure.

Other embodiments are also contemplated for uses and methods for making a package of disposable absorbent products according to any of claims 1 to 13, as described above.

From the above disclosure of the general principles of the present invention and the preceding detailed description of exemplary embodiments, those skilled in the art will readily comprehend the various modifications to which this invention is susceptible. Accordingly, this invention is intended to be limited only by the scope of the following claims and equivalents thereof.

What is claimed is:

1. A package of disposable absorbent products, comprising:

an enclosure defined by a flexible polymer material, having an interior, and including a top wall, a bottom wall disposed opposite said top wall, first and second sidewalls disposed opposite one another and extending between said top and bottom walls, and first and second end walls disposed opposite one another; and a compressed stack of disposable absorbent products in said interior and exerting an expansion force against said end walls from said interior, said compressed stack including a first disposable absorbent product contacting said first end wall from said interior, wherein:

said first end wall has a first substantially transparent portion, said first disposable absorbent product includes a first graphic display on an outer surface thereof facing said first end wall, and no portion of said first graphic display is visible through said first substantially transparent portion of said first end wall.

2. The package of claim 1, wherein said graphic display comprises a plurality of individual figures spaced from one another, none of said figures being visible through the substantially transparent portion of said first end wall.

3. The package of claim 1, wherein:
said compressed stack has a second disposable absorbent product contacting said second end wall from said interior, said second disposable absorbent product having a second graphic display on an outer surface thereof and facing said second end wall,
said second end wall has a portion that is substantially transparent, and
no portion of said second graphic display is visible through said substantially transparent portion of said second end wall.

4. The package of claim 3, wherein said first and second graphic displays are at least substantially similar.

5. The package of claim 1, wherein each of said disposable absorbent products in said stack includes a graphic display on a respective outer surface thereof at least substantially similar to said first graphic display.

6. The package of claim 1, wherein said substantially transparent portion is an elongated strip having a width no greater than about 25 mm.

7. The package of claim 6, further comprising identifying indicia on said substantially transparent portion.

8. The package of claim 1, wherein said substantially transparent portion includes a seal of said enclosure.

9. The package of claim 1, wherein at least one of said first or second sidewalls or said top or bottom walls includes a second substantially transparent portion.

10. The package of claim 1, wherein said second end wall is substantially opaque.

11. The package of claim 1, wherein each of said disposable absorbent products is selected from the group consisting of incontinence pads, feminine pads, training pants, baby diapers, and adult diapers.

12. The package of claim 11, wherein said first disposable absorbent product includes a front panel, a back panel, and a crotch panel between said front and back panels, said first graphic display being located on at least one of said front or back panels.

13. The package of claim 11, wherein said first disposable absorbent product includes a front panel, a back panel, a crotch panel between said front and back panels, and an outer wrapping element enveloping said front, back, and crotch panels, said first graphic display being located on said outer wrapping element.

14. A package of disposable absorbent products, comprising:
an enclosure defined by a flexible polymer material, having an interior, and including a top wall, a bottom wall disposed opposite said top wall, first and second sidewalls disposed opposite one another and extending between said top and bottom walls, and first and second end walls disposed opposite one another; and
a compressed stack of disposable absorbent products in said interior and exerting an expansion force against said end walls from said interior, said compressed stack including a first disposable absorbent product contacting said first end wall from said interior,
wherein:
said first end wall has an elongated strip portion that is substantially transparent,
each of said disposable absorbent products includes a graphic display on a respective outer surface thereof, said graphic display of said first disposable absorbent product facing said first end wall from said interior, and
no portion of said graphic display of said first disposable absorbent product is visible through said elongated strip portion of said first end wall.

15. The package of claim 14, further comprising indicia on said elongated strip displaying information associated with the disposable absorbent products contained in said package.

16. The package of claim 14, wherein at least one of said first or second sidewalls or said top or bottom walls includes a second portion that is substantially transparent.

17. A method of packaging a stack of compressed disposable absorbent products, at least a first one of the disposable absorbent products located at an end of the stack having a graphic display on an outer surface thereof, the method comprising:
enclosing the compressed stack with a flexible polymeric material having at least one substantially transparent portion, so as to define an enclosure having an interior and further having a top wall, a bottom wall disposed opposite the top wall, a pair of sidewalls disposed opposite one another and extending between the top and bottom walls, and a pair of end walls, the compressed stack exerting an expansion force against the end walls from the interior; and
positioning the compressed stack and flexible polymeric material relative to one another such that:
(a) the at least one substantially transparent portion is located at a first one of the end walls of the enclosure,
(b) the graphic display faces the first one of the end walls, and
(c) no portion of the graphic display is visible through the at least one substantially transparent portion.

18. The method of claim 17, further comprising:
defining a seal of the enclosure at the at least one substantially transparent portion.

19. The method of claim 17, further comprising:
displaying information on the substantially transparent portion, the information being associated with the disposable absorbent products contained within the enclosure.

20. The method of claim 17, wherein the flexible polymeric material has at least a second substantially transparent portion, the method further comprising:
positioning the compressed stack and flexible polymeric material relative to one another such that the second substantially transparent portion forms part of at least one of the top wall, bottom wall, or the sidewalls of the enclosure.

* * * * *

UNITED STATES PATENT AND TRADEMARK OFFICE
CERTIFICATE OF CORRECTION

PATENT NO. : 8,479,920 B2
APPLICATION NO. : 13/278892
DATED : July 9, 2013
INVENTOR(S) : Mariela Biber It is certified that error appears in the above-identified patent and that said Letters Patent is hereby corrected as shown below:

In the Specification:

In column 7, line 25, change "or for the substantially" to --or the substantially--;

In column 8, lines 38 and 39, change "in association with" to --in connection with--;

Delete the disclosure beginning at column 8, line 61 and ending at column 10, line 40.

In the Claims:

Column 11, lines 6-7, in claim 2, change "the substantially transparent portion" to --said first substantially transparent portion--.

Signed and Sealed this
Twentieth Day of August, 2013

Teresa Stanek Rea
*Acting Director of the United States Patent and Trademark Office*